US00PP23972P2

(12) United States Plant Patent
Mukundan

(10) Patent No.: US PP23,972 P2
(45) Date of Patent: Oct. 8, 2013

(54) ***AGLAONEMA* PLANT NAMED 'MUKROCK'**

(50) Latin Name: *Aglaonema hybrida*
Varietal Denomination: Mukrock

(75) Inventor: Parthasarathy Mukundan, Alwarpet Chennai (IN)

(73) Assignee: K.S.G.'s Farm & Nursery, Chennai (IN)

( * ) Notice: Subject to any disclaimer, the term of this patent is extended or adjusted under 35 U.S.C. 154(b) by 105 days.

(21) Appl. No.: 13/373,836

(22) Filed: Dec. 1, 2011

(51) Int. Cl.
*A01H 5/00* (2006.01)

(52) U.S. Cl.
USPC ..... Plt./376

(58) Field of Classification Search
USPC ..... Plt./376
See application file for complete search history.

*Primary Examiner* — June Hwu
(74) *Attorney, Agent, or Firm* — C. A. Whealy

(57) ABSTRACT

A new and distinct cultivar of *Aglaonema* plant named 'Mukrock', characterized by its upright and somewhat outwardly arching plant habit; freely clumping habit; vigorous and robust growth habit; relatively short internodes giving a compact, dense and full plant form; large lanceolate leaves with undulate margins that are dark green in color; dark green-colored petioles; and relative tolerance to low temperatures.

1 Drawing Sheet

Botanical designation: *Aglaonema hybrida.*
Cultivar denomination: 'MUKROCK'.

BACKGROUND OF THE INVENTION

The present invention relates to a new and distinct cultivar of *Aglaonema* plant, botanically known as *Aglaonema hybrida* and hereinafter referred to by the name 'Mukrock'.

The new *Aglaonema* plant is the product of a controlled breeding program conducted by the Inventor in Chamrajpet, Bangalore, India. The objective of the breeding program is to create new full, dense and compact *Aglaonema* plants with good plant vigor, interesting and unique leaf shapes and variegation patterns, resistance to pathogens and pests and tolerance to low temperatures.

The new *Aglaonema* plant is the product of a cross-pollination conducted by the Inventor on Mar. 6, 2004 of a proprietary selection of *Aglaonema hybrida* identified as code number AG-2004-24, not patented, as the female, or seed, parent with an unnamed selection of *Aglaonema tenuipes*, not patented, as the male, or pollen, parent. The new *Aglaonema* plant was discovered and selected by the Inventor in April, 2005 as a single plant from within the resultant progeny of the stated cross-pollination in a controlled environment in Tiruporur, Chennai, India.

Asexual reproduction of the new *Aglaonema* plant by cuttings and divisions in a controlled environment in Tiruporur, Chennai, India since September, 2005 has shown that the unique features of this new *Aglaonema* plant are stable and reproduced true to type in successive generations of asexual reproduction.

SUMMARY OF THE INVENTION

Plants of the new *Aglaonema* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'Mukrock'. These characteristics in combination distinguish 'Mukrock' as a new and distinct *Aglaonema* plant:

1. Upright and somewhat outwardly arching plant habit.
2. Freely clumping habit.
3. Vigorous and robust growth habit.
4. Relatively short internodes giving a compact, dense and full plant form.
5. Large lanceolate leaves with undulate margins that are dark green in color.
6. Dark green-colored petioles.
7. Relatively tolerant to low temperatures.

Plants of the new *Aglaonema* differ from plants of the female parent selection in the following characteristics:

1. Plants of the new *Aglaonema* are more outwardly arching than plants of the female parent selection.
2. Plants of the new *Aglaonema* are more freely clumping than plants of the female parent selection.
3. Plants of the new *Aglaonema* have larger, longer and more undulate leaves than plants of the female parent selection.
4. Plants of the new *Aglaonema* and the female parent selection differ in leaf coloration.

Plants of the new *Aglaonema* differ from plants of the male parent selection in the following characteristics:

1. Plants of the new *Aglaonema* are more upright than and are not as compact as plants of the male parent selection.
2. Plants of the new *Aglaonema* are more freely clumping and denser and fuller than plants of the male parent selection.
3. Plants of the new *Aglaonema* have larger and more undulating leaves than plants of the male parent selection.
4. Plants of the new *Aglaonema* and the male parent selection differ in leaf shape and color.

Plants of the new *Aglaonema* can be compared to plants of *Aglaonema hybrida* 'Maria', not patented. In side-by-side comparisons conducted in Chamrajpet, Bangalore, India, plants of the new *Aglaonema* differed from plants of 'Maria' in the following characteristics:

1. Plants of the new *Aglaonema* were more freely clumping and denser and fuller than plants of 'Maria'.
2. Plants of the *Aglaonema* were faster growing than plants of 'Maria'.
3. Plants of the new *Aglaonema* had larger and more undulating leaves than plants of 'Maria'.
4. Plants of the new *Aglaonema* and 'Maria' differed in leaf shape and color.
5. Plants of the new *Aglaonema* were more low temperature tolerant than plants of 'Maria'.

Plants of the new *Aglaonema* can be compared to plants of *Aglaonema hybrida* 'Green Majesty', disclosed in U.S. Plant Pat. No. 9,069. In side-by-side comparisons conducted in Chamrajpet, Bangalore, India, plants of the new *Aglaonema* differed from plants of 'Green Majesty' in the following characteristics:

1. Plants of the new *Aglaonema* were more compact, freely clumping and denser and fuller than plants of 'Green Majesty'.
2. Plants of the *Aglaonema* were faster growing than plants of 'Green Majesty'.
3. Plants of the new *Aglaonema* had larger and more undulating leaves than plants of 'Green Majesty'.
4. Plants of the new *Aglaonema* and 'Green Majesty' differed in leaf shape and color.
5. Plants of the new *Aglaonema* and 'Green Majesty' differed in leaf petiole color.

BRIEF DESCRIPTION OF THE PHOTOGRAPH

The accompanying photograph illustrates the overall appearance of the new *Aglaonema* plant showing the colors as true as it is reasonably possible to obtain in colored reproductions of this type. Colors in the photograph may differ slightly from the color values cited in the detailed botanical description which accurately describe the colors of the new *Aglaonema* plant.

The photograph comprises a side perspective view of a typical plant of 'Mukrock' grown in a container.

DETAILED BOTANICAL DESCRIPTION

The aforementioned photographs and following observations and measurements describe plants grown in 25-cm containers in Miami, Fla. during the summer and autumn in a polypropylene-covered shadehouse. Plants were grown under environmental conditions and cultural practices which approximate those generally used in commercial *Aglaonema* production. During the production of the plants, day temperatures ranged from 27° C. to 37° C., night temperatures ranged from 15° C. to 26° C. and light levels averaged 1,500 foot-candles. Plants were one year old when the photographs and the detailed description were taken. In the following description, color references are made to The Royal Horticultural Society Colour Chart, 2007 Edition, except where general terms of ordinary dictionary significance are used.

Botanical classification: *Aglaonema hybrida* 'Mukrock'.

Parentage:

*Female, or seed, parent.*—Proprietary selection of *Aglaonema hybrida* identified as code number AG-2004-24, not patented.

*Male, or pollen, parent.*—Unnamed selection of *Aglaonema tenuipes*, not patented.

Propagation:

*Type.*—By cuttings and divisions.

*Time to initiate roots, summer.*—About 21 to 28 days at 25° C. to 32° C.

*Time to initiate roots, winter.*—About 30 to 40 days at 12° C. to 25° C.

*Time to produce a rooted young plant, summer.*—About 30 to 35 days at 25° C. to 32° C.

*Time to produce a rooted young plant roots, winter.*—About 45 to 60 days at 12° C. to 25° C.

*Root description.*—Fleshy, medium in thickness; off-white in color.

*Rooting habit.*—Freely branching; profuse, high density.

Plant description:

*Plant and growth habit.*—Upright and somewhat outwardly arching plant habit; freely clumping habit; relatively short internodes giving a compact, dense, full and symmetrical habit; vigorous growth habit; developing leaves initially upright, then arching outwardly with development.

*Plant height, from soil level to top of leaf plane.*—About 46 cm.

*Plant diameter or spread.*—About 70 cm.

*Stem description.*—Clumping habit: Plants of the new *Aglaonema* are freely clumping with about twelve clumps developing per plant. Aspect: Mostly upright. Strength: Strong; somewhat flexible. Diameter, at the base: About 1.8 cm. Internode length, at the base: About 1.5 cm. Color: Darker than N137A.

Foliage description:

*Arrangement.*—Alternate to whorled; simple.

*Length.*—About 23.5 cm.

*Width.*—About 6.5 cm.

*Shape.*—Narrowly lanceolate.

*Apex.*—Acuminate, straight.

*Base.*—Cordate with oblique tendencies.

*Margin.*—Entire; undulate.

*Texture, upper and lower surfaces.*—Smooth, glabrous.

*Venation pattern.*—Pinnate.

*Color.*—Developing leaves, upper surface: More green than 146A; venation, close to more green than 146A. Developing leaves, lower surface: Closest to 146B; venation, closest to 146B. Fully expanded leaves, upper surface: Darker than N137A; venation, darker than N137A. Fully expanded leaves, lower surface: Closest to N137B; venation, closest to N137B.

*Petiole.*—Aspect: Mostly erect, outwardly arching with development. Length: About 14 cm. Diameter, distal: About 4.5 mm. Diameter, proximal, flattened: About 2.4 cm. Strength: Strong; flexible. Color, distal: Close to N137A. Color, proximal: Close to N137A to N137B; area adjacent to stem, close to 157A to 157C. Wing length: About 10 cm. Wing diameter, base: About 4 mm. Wing color, inner and outer surfaces: Close to N137A; towards the base, close to N137B; area adjacent to stem, close to 157A to 157C.

Inflorescence description: Inflorescence development has not been observed on plants of the new *Aglaonema*.

Disease & pest resistance: Plants of the new *Aglaonema* have not been observed to be resistant to pathogens or pests common to *Aglaonema*.

Temperature tolerance: Plants of the new *Aglaonema* have been observed to be relatively low temperature tolerant and to tolerate temperatures ranging from about 15° C. to about 40° C.

It is claimed:

1. A new and distinct *Aglaonema* plant named 'Mukrock' as illustrated and described.

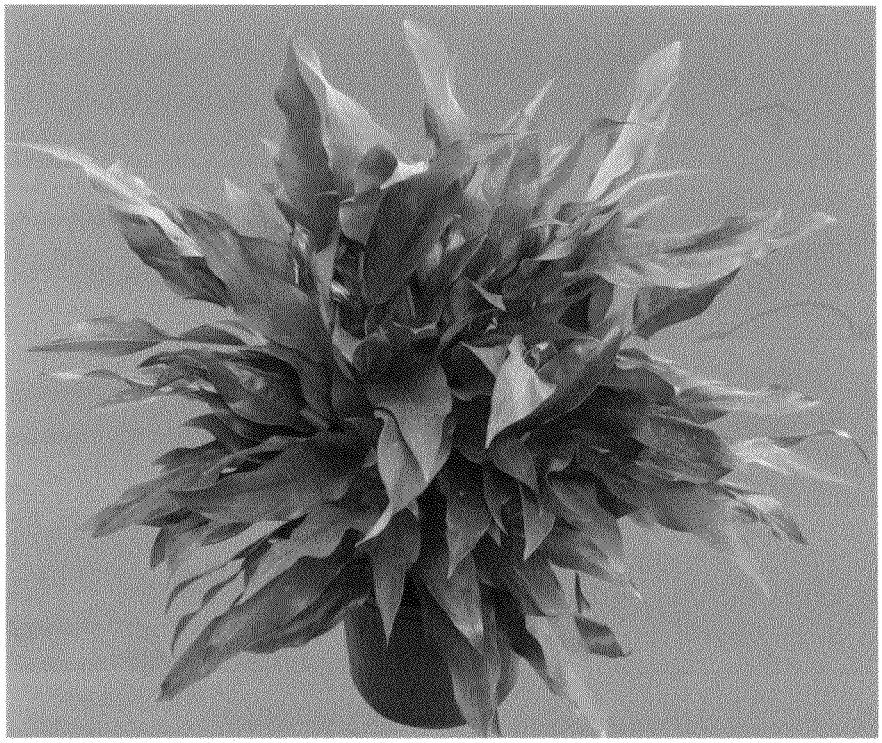

* * * * *